United States Patent [19]

Nishida et al.

[11] Patent Number: 5,304,684
[45] Date of Patent: Apr. 19, 1994

[54] PROCESS FOR PRODUCING PHENOL AND METHYL ETHYL KETONE

[75] Inventors: Hiroshi Nishida; Kazuo Kimura, both of Ichihara; Shouji Hamada, Misawa; Masaaki Toma, Ichihara; Hirooki Nagaoka, Minoo, all of Japan

[73] Assignee: Sumitomo Chemical Company, Ltd., Osaka, Japan

[21] Appl. No.: 86,896

[22] Filed: Jul. 7, 1993

[30] Foreign Application Priority Data

Jul. 7, 1992 [JP] Japan ................... 4-179711
Dec. 24, 1992 [JP] Japan ................... 4-344333
Mar. 5, 1993 [JP] Japan ................... 5-04493

[51] Int. Cl.$^5$ ............................... C07C 45/53
[52] U.S. Cl. ........................... 568/385; 568/410; 568/754; 568/798
[58] Field of Search ............ 568/385, 410, 411, 798, 568/754

[56] References Cited

U.S. PATENT DOCUMENTS

| | | | |
|---|---|---|---|
| 2,904,592 | 9/1959 | Ellis et al. | 568/385 |
| 2,906,676 | 9/1959 | Bewley et al. | 568/385 |
| 2,957,921 | 10/1960 | Adams et al. | 568/385 |
| 3,215,745 | 11/1965 | Frank | 568/410 |
| 3,309,407 | 3/1967 | Carpenter et al. | 568/385 |
| 4,006,194 | 2/1977 | Luberoff et al. | 568/385 |
| 4,434,305 | 2/1984 | Kurosaka et al. | 568/385 |
| 4,626,600 | 12/1986 | Fulmer et al. | 568/385 |

FOREIGN PATENT DOCUMENTS 58-208246 12/1983 Japan ................... 568/385

*Primary Examiner*—James H. Reamer
*Attorney, Agent, or Firm*—Cushman, Darby & Cushman

[57] ABSTRACT sec-Butylbenzene hydroperoxide obtained by oxidizing sec-butylbenzene is decomposed into phenol and methyl ethyl ketone, a resulting liquid comprising a methyl ethyl ketone as the main component is washed with an aqueous alkali solution to remove carboxylic acids, carboxylic acid esters, unsaturated ketones, and aldehydes, and the washed liquid is further subjected to neutralization, dehydration, and distillation.

A methyl ethyl ketone can be obtained which has a high quality with regard to purity and potassium permanganate fading.

7 Claims, No Drawings

PROCESS FOR PRODUCING PHENOL AND METHYL ETHYL KETONE

The present invention relates to a process for producing phenol and methyl ethyl ketone. In more particular, it relates to a process for producing phenol and methyl ethyl ketone from sec-butylbenzene used as the starting material.

There is already known a technique which comprises oxidizing sec-butylbenzene into sec-butylbenzene hydroperoxide and then decomposing the sec-butylbenzene hydroperoxide with sulfuric acid to form phenol and methyl ethyl ketone (JP-A-48-80524).

One of the quality standards required of methyl ethyl ketone is a standard regarding to its purity and potassium permanganate fading (JIS K 8900). The methyl ethyl ketone obtained by the aforesaid technique has a problem of having difficulty in meeting the above-mentioned standard regarding to purity and potassium permanganate fading.

For purifying methyl ethyl ketone, the following processes are known heretofore. JP-B-45-41205 discloses a process which comprises decomposing t-butanol, which forms an azeotropic mixture with methyl ethyl ketone, into isobutylene by using a zeolite catalyst and then separating it from methyl ethyl ketone. JP-B-57-35167 discloses a process for improving the potassium permanganate fading of crude methyl ethyl ketone by bringing it into contact with hydrogen in the presence of a catalyst containing rhodium or platinum. Further, JP-B-47-33323 discloses a process of removing aldehydes contained in methyl ethyl ketone by forming adducts of the aldehyde with an alkali metal hydrogen-sulfite alkali metal sulfite. These processes, however, do not give a sufficient purification effect when applied to the above-mentioned technique of obtaining phenol and methyl ethyl ketone from sec-butylbenzene used as the starting material.

Accordingly, the object of the present invention is to provide a process for producing phenol and methyl ethyl ketone which comprises oxidizing sec-butylbenzene into sec-butylbenzene hydroperoxide and then decomposing the sec-butylbenzene hydroperoxide with the aid of an acidic catalyst to form phenol and methyl ethyl ketone which process can give a high quality methyl ethyl ketone.

The present inventors have made extensive study on factors which exert an influence on the purity and potassium permanganate fading of methyl ethyl ketone. As the result, it has been found out that the main substances which exert an influence on purity are phenol, sec-butylbenzene, carboxylic acids, carboxylic acid esters, water, ethanol and acetone, and the main substances which exert an influence on potassium permanganate fading are unsaturated ketones and aldehydes. Further, the present inventors have made extensive study to find a process for efficiently removing such specific impurities and resultantly have attained the present invention.

Thus, the present invention relates to a process for producing phenol and methyl ethyl ketone from sec-butylbenzene used as the starting material which process comprises the following steps:

an oxidation step (A): a step of oxidizing sec-butylbenzene to obtain an oxidation reaction liquid comprising sec-butylbenzene hydroperoxide as the main component, a concentration step (B): a step of concentrating the oxidation reaction liquid by distillation to obtain from the column bottom a bottom liquid comprising sec-butylbenzene hydroperoxide as the main component and from the column top a distillate comprising sec-butylbenzene as the main component, and recycling the distillate to the oxidation step (A), a decomposition step (C): a step of bringing the bottom liquid of the concentration step (B) into contact with an acidic catalyst to decompose the sec-butylbenzene hydroperoxide thereby to obtain a decomposition liquid containing phenol and methyl ethyl ketone, the first neutralization step (D): a step of neutralizing the decomposition liquid with an aqueous alkali solution, then separating the resulting mixture into an oil layer and an aqueous layer, and recycling a part of the aqueous layer to the neutralization step (D), the first distillation step (E): a step of subjecting the oil layer obtained in the first neutralization step (D) to distillation to obtain a bottom liquid comprising phenol as the main component and a distillate comprising methyl ethyl ketone as the main component, an alkali-washing step (F): a step of washing the distillate obtained in the first distillation step (E) with an aqueous alkali solution to remove carboxylic acids, carboxylic acid esters, unsaturated ketones, and aldehydes, and then separating the resulting liquid mixture into an oil layer and an aqueous layer, the second neutralization step (G): a step of neutralizing the oil layer obtained in the alkali-washing step (F) and then separating the resulting liquid mixture into an oil layer and an aqueous layer, the first purification step (H): a step of subjecting the oil layer obtained in the second neutralization step (G) to distillation to obtain a bottom liquid comprising methyl ethyl ketone as the main component and an overhead liquid container water, and the second purification step (I): a step of subjecting the bottom liquid obtained in the first purification step (H) to distillation to recover methyl ethyl ketone as a bottom liquid and recycling a overhead liquid to the alkali-washing step (F).

The process of the present invention is described in detail below.

The oxidation step (A) of the present invention is a step of oxidizing sec-butylbenzene to obtain an oxidation reaction liquid comprising sec-butylbenzene hydroperoxide as the main component and is conducted, for example, as follows. Liquid sec-butylbenzene is made to contact with an oxygen-containing gas at a temperature of 90°–150° C. and a pressure of 1–10 k/cm$^2$ G to form sec-butylbenzene hydroperoxide.

The concentration step (B) of the present invention is a step of concentrating the oxidation reaction liquid of the step (A) by distillation to obtain from the column bottom a bottom liquid comprising sec-butylbenzene hydroperoxide as the main component and from the column top a distillate comprising sec butylbenzene as the main component. The conditions of distillation in the concentration step (B) are to be set, in short, so as to give a bottom liquid comprising sec-butylbenzene hydroperoxide as the main component and a distillate comprising sec-butylbenzene as the main component; they may be, for example, a column bottom temperature of 50°–150° C. and a column top pressure of 1–200 torr.

The decomposition step (C) of the present invention is a step of bringing the bottom liquid of the concentration step (B) into contact with an acidic catalyst to decompose sec-butylbenzene hydroperoxide thereby to obtain a decomposition liquid containing phenol and methyl ethyl ketone. The acidic catalyst used may be sulfuric acid, sulfuric acid anhydride, perchloric acid, phosphoric acid, or the like. The acidic catalyst is used in an amount of usually 0.01–1% by weight. The decomposition temperature is usually in the range of 50°–100° C.

The first neutralization step (D) of the present invention is a step of neutralizing the decomposition liquid obtained in the decomposition step (C) with an aqueous alkali solution, then separating the resulting liquid mixture onto an oil layer and an aqueous layer, and recycling a part of the aqueous layer to the neutralization step. The alkalis used for neutralization may be the hydroxides, carbonates, bicarbonates, and the like of sodium, potassium, lithium, and the like. The alkali is used in an amount sufficient for keeping the pH of the aqueous layer usually at 5–11, preferably at 6–10. The temperature is usually from ordinary temperature to 90° C. The weight ratio of the oil layer to the aqueous layer is preferably 0.5–5. The apparatus used is selected so that it may ensure a thorough contact of the liquid layer to be neutralized with the aqueous alkali solution and subsequent separation of the oil layer from the aqueous layer; it may be, for example, a vessel equipped with a stirrer, line mixer, pipe mixer, or the like. In the first neutralization step (D), it is preferable, in order to decrease the amount of waste water, that a part of the aqueous layer once used in the neutralization step is recycled to the neutralization step and used again. Though the salt concentration in the neutralization step increases resultantly, it is preferably maintained usually at 1–30% by weight. The oil layer obtained in the first neutralization step (D) is sent to the subsequent first distillation step (E), while the aqueous layer (or, when a part thereof has been recycled, the remaining aqueous layer) is discarded.

The first distillation step (E) of the present invention is a step of subjecting the oil layer obtained in the first neutralization step (D) to distillation to obtain a bottom liquid comprising phenol as the main component and a distillate comprising methyl ethyl ketone as the main component. The distillation conditions may be, for example, a column bottom temperature of 150°–200° C. and a column top pressure of from normal pressure to 500 torr. Further, in order to prevent the sec-butylbenzene contained in the first distillation column feed from leaking to the distillate side, the concentration of methyl ethyl ketone in the first distillation column feed is preferably made high. For example, it is also possible to recycle and feed a part of the methyl ethyl ketone obtained in the third distillation step (Ib) described later to the above-mentioned first distillation column.

The alkali-washing step (F) of the present invention is a step of washing the distillate obtained in the first distillation step (E) with an aqueous alkali solution to remove carboxylic acids, carboxylic acid esters, unsaturated ketones, and aldehydes. The alkalis used maybe the oxides, carbonates, bicarbonates, and the like of sodium, potassium, lithium, and the like. The alkali is used in an amount which will give a pH of the oil layer in the alkali-washing step of usually 7 or more, preferably 10–14, more preferably 13–14. When the pH of the oil layer is too low, the removal of carboxylic acids, carboxylic acid esters, unsaturated ketones, and aldehydes tends to be insufficient. The alkali is preferably used as an aqueous solution, the concentration of which is preferably 10–48% by weight. The weight ratio of the oil layer to the aqueous layer in the alkali-washing step is 0.5–10, preferably 0.5–4. The weight ratio of the oil layer to the aqueous layer and the pH of the oil layer in the alkali-washing step are closely correlated with the conversion of isobutyraldehyde, which adversely affects the potassium permanganate fading. That is, when the pH is the same, a lower weight ratio of the oil layer to the aqueous layer results in a higher conversion of isobutyraldehyde; when the weight ratio of the oil layer to the aqueous layer is the same, a higher pH results in a higher conversion of isobutyraldehyde. Therefore, by selecting, within a range permissible from volume efficiency, a low weight ratio of the oil layer to the aqueous layer and a high pH, isobutyraldehyde can be efficiently converted and removed. The apparatus used is selected so that it may ensure a thorough contact and reaction of the oil to be washed with the aqueous alkali solution and subsequent separation of the oil layer from the aqueous layer; it may be, for example, a vessel equipped with a stirrer. More preferably, a continuous mixing vessel equipped with plural stirrers or a reaction apparatus of liquid-liquid extraction type is used.

The alkali-washing step (F) is a particularly important step in the present invention. That is, substantially the whole of the carboxylic acids, carboxylic acid esters and unsaturated ketones and most of the aldehydes contained in the distillate obtained in the first distillation step (E) are removed in this alkali-washing step. The contents of the carboxylic acids, carboxylic acid esters, and unsaturated ketones can be reduced respectively to about 0.1 ppm by weight or less. The content of the aldehydes can also be reduced to about 10 ppm by weight or less by appropriate selection of the weight ratio of the oil layer to the aqueous layer and the pH. In this alkali-washing step, however, it suffices to reduce the content of aldehydes to about 400 ppm by weight. The aldehydes can be separated in the third distillation step (Ib) described later to a level that passes the potassium permanganate fading test.

The carboxylic acids referred to herein are mainly acetic acid and formic acid, which cause the problem of corrosion of the production apparatus. The carboxylic acid esters herein are mainly ethyl acetate and ethyl formate. In particular, ethyl acetate has a problem of being insufficiently removable by distillation alone. The unsaturated ketones herein refer mainly to methyl vinyl ketone. When methyl ethyl ketone contains even as low as 1 ppm by weight of methyl vinyl ketone, it cannot pass the potassium permanganate fading test. Furthermore, methyl vinyl ketone has a boiling point differing by only 2° C. from that of methyl ethyl ketone and hence can hardly be separated economically from the latter ketone by distillation. The aldehydes herein are mainly acetaldehyde and isobutyraldehyde, of which isobutyraldehyde has a boiling point near to that of methyl ethyl ketone and cannot be sufficiently separated economically by distillation alone. When methyl ethyl ketone contains even as low as about 50 ppm by weight of isobutyraldehyde, the ketone cannot pass the potassium permanganate fading test. Further, in the alkali-washing step (F), 3-methyl-3-buten-2-one is newly formed from methyl ethyl ketone and formaldehyde. When 3-methyl-3-buten-2-one is present in methyl ethyl ketone even in as low an amount as 2 ppm by weight, the methyl ethyl ketone does not pass the potassium permanganate fading test, but the unsaturated ketone can be separated in the second purification step (I) subsequent to the alkali washing.

The second neutralization step (G) of the present invention is a step of neutralizing the oil layer which has been subjected to the alkali-washing. In more particular, it is a step of neutralizing the oil layer after alkali washing with an aqueous sulfuric acid solution and separating the resulting liquid mixture into an oil layer and an aqueous layer. The neutralization is preferably conducted because the pH of the oil layer after alkali washing is an important factor in the subsequent second distillation step (Ia). That is, in the alkali washing, a dimer adduct of aldol condensation type is formed from methyl ethyl ketone and isobutyraldehyde of an impurity. During the second distillation, in an alkaline region of a pH of 10 or more, a backward decomposition reaction of the dimer adduct takes place to regenerate isobutyraldehyde, and resultantly an increased amount of isobutyraldehyde gets mixed into the distillate of the initial distillation stage. As mentioned above, isobutyraldehyde is a substance which causes potassium permanganate fading. Moreover, in batch distillation the regeneration of the aldehyde is recognized in the initial stage distillate to cause the lowering of the recovery of the intended ketone and, in continuous distillation it causes the lowering of the yield. To prevent the decrease of the yield of methyl ethyl ketone which meets the requirements specified in JIS, it is desirable to suppress the backward decomposition reaction of the dimer adduct. On the other hand, in a neutral or acidic region of a pH of 7 or lower, virtually no backward decomposition reaction takes place and resultantly substantially no contamination of the distillate by isobutyraldehyde occurs. Therefore, in the distillation of the oil layer after alkali washing, the contamination of the distillate by isobutyraldehyde can be prevented by neutralizing the oil layer before the distillation.

The acids used for the neutralization may be sulfuric acid, hydrochloric acid, nitric acid, and the like. The acid is used in an amount sufficient for keeping the pH of the aqueous layer usually at 7 or less, preferably at 6–4. The temperature is from room temperature to 90° C., preferably 60°–80° C. The weight ratio of oil layer to the aqueous layer is preferably 0.5–4. The apparatus used is selected such that it may ensure a thorough contact of the oil layer to be neutralized with the aqueous acid solution and subsequent separation of the oil layer from the aqueous layer; it may be, for example, a vessel equipped with a stirrer, line mixer, pipe mixer, etc.

In the second neutralization step (G), it is desirable, in order to decrease the amount of waste water, to recycle a part of the aqueous layer used in the neutralization step and use it again in the neutralization step. As the result, the salt concentration in the second neutralization step increases. The salt concentration is desirably kept usually at 0.5–15% by weight, preferably at 2–10% by weight.

In the present invention, further, it is preferable to interpose a water-washing step, which is a step of water-washing the oil layer obtained in the second neutralization step (G), between the second neutralization step (G) and the first purification step (H). The temperature in the water washing is from room temperature to 90° C., preferably 60°–80° C., and the weight ratio of the oil layer to the aqueous layer is preferably 1–4. The apparatus used is selected so that it may ensure a thorough contact of the oil layer to be water-washed with washing water and subsequent separation of the oil layer from the aqueous layer; it may be, for example, a vessel equipped with a stirrer, line mixer, pipe mixer, and the like. By the use of such a water-washing step, the precipitation and deposition of various salts in the subsequent distillation column can be prevented and a stable, long-period running of the distillation column becomes possible.

The first purification step (H) of the present invention is a step of removing water from the oil layer obtained in the second neutralization step (G). More specifically, it is a step of adding a third substance called an entrainer to the oil layer obtained in the second neutralization step (G), subjecting the resultant liquid mixture to a heterogeneous azeotropic distillation, and removing a liquid mixture of water and lower boiling point components from the column top. The "lower boiling point components" herein refer to components having lower boiling points than methyl ethyl ketone, and include acetone and ethanol. As the entrainer, there may be used a component which undergoes liquid-liquid phase separation with water and which has a lower boiling point than methyl ethyl ketone or forms a minimum temperature azeotropic mixture with methyl ethyl ketone. Specific examples thereof include hexane, cyclohexane, and heptane.

As to the removal of water, a process has hitherto been used industrially in which two distillation columns, one operated at a high pressure of about 5–20 $kg/cm^2$ G and one operated in the neighborhood of normal pressure, are used and methyl ethyl ketone is obtained from the bottom of the high pressure column and water from the bottom of the low pressure column (this process being hereinafter referred to as the high pressure process). However, the oil layer obtained in the second neutralization step (G) or the oil layer which has been treated in the water-washing step of the present invention contains, besides methyl ethyl ketone, hydrophilic lower boiling point components including acetone and ethanol; in the high pressure process, these lower boiling point components accumulate at the column top. Though the lower boiling point components can be removed by purging a part of the column top liquid, when the concentration of the lower boiling point components in the column top liquid becomes too high, the liquid in the column comes to undergo no liquid-liquid phase separation. As a consequence, the amount of the liquid to be purged becomes large. In actuality, therefore, the high pressure process can be hardly adopted in the present invention.

JP-A-59-166205 discloses an example of a heterogeneous azeotropic distillation which uses an entrainer in the dehydration of methyl ethyl ketone and describes that water in methyl ethyl ketone can be removed by using this method. The first purification step (H) of the present invention, on the other hand, is featured in that an azeotropic distillation is conducted by using an entrainer not only to effect dehydration but also simultaneously to remove impurities contained in the oil layer and having lower boiling points than methyl ethyl ketone, including acetone and ethanol, in a form dissolved in the distillate. The entrainer is preferably hexane, cyclohexane, or heptane, more preferably hexane. The distillation conditions in the first purification step (H) may be, for example, a column bottom temperature of 85° C. and a column top pressure of from normal pressure to 20 $kg/cm^2$. The distillation can reduce the water content of the oil layer from 10% by weight down to 300 ppm by weight and further can remove 80-90% of acetone and methanol.

The second purification step (I) of the present invention is a step of distilling the bottom liquid obtained in the first purification step (H) to recover methyl ethyl ketone and recycling the overhead liquid to the alkali-washing step (F). In a preferred embodiment of the second purification step (I), it comprises the second distillation step (Ia) and the third distillation step (Ib) described below.

The second distillation step (Ia): a step of distilling the bottom liquid obtained in the first purification step (H) to remove a tarry substance containing 3-methyl-3-buten-2-one as the bottom liquid.

The third distillation step (Ib): a step of distilling the overhead liquid obtained in the second distillation step (Ia) to recover methyl ethyl ketone as the bottom liquid and recycling the newly obtained overhead liquid to the alkali-washing step (F).

The second distillation step (Ia) is a step of distilling the bottom liquid obtained in the first purification step (H) to remove a tarry substance containing 3-methyl-3-buten-2-one as the bottom liquid. In the bottom liquid obtained in the first purification step (H), a tarry substance exists which contains 3-methyl-3-buten-2-one formed in the alkali-washing step (F) and aldol condensation products of methyl ethyl ketone, aldehydes and unsaturated ketones. In particular, 3-methyl-3-buten-2-one is a potassium permanganate-fading substance, and its content should be restricted to 1 ppm by weight or less. The present distillation can reduce the content to 1 ppm by weight or less and can also remove the tarry substance completely. Thus, it can attain the improvement of the purity of methyl ethyl ketone and the removal of potassium permanganate-fading substance. The distillation may be a normal pressure distillation at a column bottom temperature of 85°-125° C. The bottom liquid is removed out of the system as a waste oil. The bottom liquid contains the dimer of methyl ethyl ketone formed in the alkali-washing step (F), the major portion of which remains as it was formed by addition reaction, without undergoing dehydration. When the bottom liquid is subjected to alkali washing again at an increased concentration, methyl ethyl ketone is regenerated by backward reaction. Therefore, if desired, a part of the bottom liquid may be recycled to the alkali-washing step (F).

The third distillation step (Ib) is a step of distilling the overhead liquid obtained in the second distillation step (Ia) to recover methyl ethyl ketone and recycling the newly obtained overhead liquid to the alkali-washing step (F). The overhead liquid obtained in the second distillation step (Ia) is completely free from impurities heavier than methyl ethyl ketone, but it contains aldehydes which are not removed completely in the alkali-washing step (F) as well as impurities having lower boiling points than methyl ethyl ketone, including acetone, ethanol and water, which are not removed completely in the first purification step (H). In the third distillation step (Ib), these lower boiling point impurities are removed and methyl ethyl ketone of a high quality (meeting the requirements specified in JIS) can be separated and recovered. Isobutyraldehyde is removed to the intended or even lower concentration, substantially the whole of the potassium permanganate-fading substances are removed, and the resulting product passes the fading test. The distillation may be, for example, a normal pressure distillation at a column bottom temperature of 82° C. The overhead liquid which contains isobutyraldehyde is recycled to the alkali-washing step (F). At this time, methyl ethyl ketone which has leaked to the distillate side can be recovered, and impurities having lower boiling points than methyl ethyl ketone are removed, via the alkali-washing step (F) and the second neutralization step (G), out of the system as the overhead liquid of the first purification step (H).

As set forth above, according to the present invention, methyl ethyl ketone can be obtained which has very low contents of phenol, sec-butylbenzene, as well as carboxylic acids, carboxylic acid esters, unsaturated ketones, aldehydes, lower boiling point components, namely ethanol and acetone, and water and has a high quality with respect to purity and potassium permanganate fading.

The present invention will be described further in detail below with reference to Examples.

EXAMPLE 1

An oil layer liquid of the first neutralization step (D) was obtained, via the oxidation step (A), the concentration step (B), the decomposition step (C) and the first neutralization step (D), which liquid contained 26.1% of methyl ethyl ketone, 24.4% of sec-butylbenzene and 33.5% of phenol.

Then, 184 kg of the oil layer liquid was distilled at normal pressure and a column bottom temperature of 177° C. to obtain 54.4 kg of a distillate containing 89.0% of methyl ethyl ketone and 119.70 kg of a bottom liquid containing 49.3% of phenol (the first distillation step (E)). Then, 50 kg of a 20% by weight aqueous sodium hydroxide solution was added to 50 kg of the above distillate and stirred at 70° C. for 2 hours to effect alkali washing (the alkali-washing step (F)). Ethyl formate, ethyl acetate, and methyl vinyl ketone were undetectable and the concentrations of 3-methyl-3-buten-2-one, isobutyraldehyde, and tarry substance were, respectively, 200 ppm by weight, 0.04% by weight, and about 1% by weight. Then 5.1 kg of an 8% aqueous sodium sulfate solution was added to 20.4 kg of the oil layer after alkali washing, 0.05 kg of a 10% by weight aqueous sulfuric acid solution was further added thereto and stirred at 70° C. for 5 minutes to obtain a pH of 7 (the second neutralization step (G)). Further, 10.4 kg of water was added to the neutralized oil layer and stirred at 70° C. for 10 minutes to effect the water-washing step. The oil layer liquid washed with water contained 10% by weight of water, 0.16% by weight of acetone, 0.27% by weight of ethanol, 0.04% by weight of isobutyraldehyde, 0.02% by weight of 3-methyl-3-buten-2-one, and about 1% by weight of tarry substance. The oil layer liquid was first distilled at normal pressure (column bottom temperature: 85° C.) with hexane added as an entrainer, to obtain a bottom liquid containing 290 ppm by weight of water, 0.01% by weight of acetone, and 0.02% by weight of ethanol (the first purification step (H)). The bottom liquid was further distilled at normal pressure (column bottom temperature 85°-125° C.) to remove 3-methyl-3-buten-2-one and the tarry substance completely (the second distillation step (Ia)), and the distillate was subjected to normal pressure distillation (column bottom temperature: 82° C.) to obtain as the side cut liquid methyl ethyl ketone of a purity of 99.982% by weight (the third distillation step (Ib)). The methyl ethyl ketone thus obtained meets the requirements specified in JIS also with regard to potassium permanganate fading.

As described above, according to the present invention, in a process for producing phenol and methyl ethyl ketone from sec-butylbenzene used as the starting material, a high quality methyl ethyl ketone could be obtained which can fully meet the requirements regarding to purity and potassium permanganate fading specified in JIS.

The quality standards specified in JIS K 8900 are as follows. Quantity

Methyl ethyl ketone, when tested in accordance with the test methods described in Test method below, shall conform to the requirements specified in the following Table.

TABLE

| Item | Guaranteed reagent grade |
|---|---|
| Appearance of aqueous solution | Within limit |
| Specific gravity (20/20° C.) | 0.804–0.808 |
| Fraction of distillate (79.0–80.5° C.) (v/v %) | 97 or more |
| Refractive index $n_D^{20}$ | 1.378–1.381 |
| Moisture (%) | 0.1 or less |
| Nonvolatile matter (%) | 0.001 or less |
| Acid | Within limit (about 0.005% or less as $CH_3COOH$) |
| Alkali | Within limit (about 0.001% or less as $NH_3$) |
| Permanganate reducible substance | Within limit |
| Sulfuric acid coloring substance | Within limit |

Test Method

Methyl ethyl ketone shall be tested in accordance with the methods described in the following.

(1) Appearance of aqueous solution, within limit

Methyl ethyl ketone (5 ml) + water (⟶25 ml)
clear and transparent (2) Specific gravity (20/20° C.), 0.804–0.808

This is determined according to 3.2.1 of JIS K 0061 (method of determination of specific gravity of chemical products)

(3) Fraction of distillate (79.0°–80.5° C.), 97 v/v % or more

This is determined according to 3.2. of JIS K 0066 (method of distillation test of chemical products).

(4) Refractive index $n_D^{20}$, 1.378–1.381

This is determined according to JIS K 0062 (method of determination of refractive index of chemical products).

(5) Moisture, 0.1% or less

Methyl ethyl ketone (10 g, about 12 ml)→determination according to 2.1(4)(a) of JIS K 0068 (method of testing moisture in chemical products), with the exception that 12 ml of pyridine-ethylene glycol mixture (10 ml of pyridine+2 ml of ethylene glycol) is used in place of about 25 ml of methanol (for Karl Fischer's reagent).

(6) Nonvolatile matter, 0.001% or less

Methyl ethyl ketone (100 g, about 124 ml)⟶ evaporation to dryness on water bath⟶ drying at 110° C.

residue: 1 mg or less (7) Acid, within limit (about 0.005% or less as $CH_3COOH$)

"Alkali" specified in (8) below shall be tested simultaneously.

Methyl ethyl ketone (25 ml) is placed in a 300-ml universal ground glass joint conical flask to which nitrogen was passed beforehand for about 2 minutes to replace air. Water (200 ml) free from carbonic acid is added thereto (quickly). A bromothymol blue solution (0.04 w/v %) for pH test (6 drops) is added. The resulting solution is neutralized with N/20 sodium hydroxide solution or N/20 hydrochloric acid while passing nitrogen over the liquid surface until the color of the solution reaches the intermediate color[1] (namely, the color of buffer solution of pH 6.8). Then, methyl ethyl ketone (20 g, about 25 ml) is added and the resulting solution is tested as follows.

(a) When the solution shows a color in the range from the intermediate color[1] to an acidic color (yellow color):

a N/20 sodium hydrochloride solution (0.34 ml[2]) is added to the solution while passing nitrogen over the solution surface.—The resulting solution shall show a color in the range from the intermediate color[1] to the alkaline color (blue color)

(b) When the solution shows a color in the range from the intermediate color[1] to an alkaline color (blue color):

a N/20 hydrochloric acid (0.24 ml[2]) is added to the solution while passing nitrogen over the solution surface.—The resulting solution shall show a color in the range from the intermediate color[1] to an acidic color (yellow color).

Note:
1) The color developed when a buffer solution (225 ml) of pH 6.8 specified in 16.2 (d) of JIS K 8004 (general methods for testing reagent chemicals) is placed in the same vessel as described in the test (in the operation of (a) or (b), 25 ml of the buffer solution is further added) and the bromothymol blue solution for pH test (0.04 w/v %) (6 drops) is added thereto.

2) The solutions are added by using a micro-buret of a minimum graduation of 0.01 ml.

Remarks for reference:

One milliliter of N/20 sodium hydroxide solution corresponds to 0.0030 g of $CH_3COOH$.

One milliliter of N/20 hydrochloric acid corresponds to 0.00085 g of $NH_3$.

(8) Alkali, within limit (about 0.001% or less as $NH_3$)

"Alkali" is tested simultaneously with "acid" of (7) above.

(9) Permanganate reducible substance, within limit

Methyl ethyl ketone (30 ml)+N/10 potassium permanganate solution (0.5 ml)→shaking→standing at about 15° C. for 10 minutes—The mixture shall keep a pink color.

(10) Sulfuric acid coloring substance, within limit

Methyl ethyl ketone (5 ml)→Cooling to 10° C.+sulfuric acid (95%) (5 ml) cooled at 10° C.→Standing at 10° C. for 5 minutes—The mixture shall show a color not deeper than the colorimetric standard solution K specified in JIS K 8004.

What is claimed is:

1. A process for producing phenol and methyl ethyl ketone from sec-butylbenzene used as the starting material which comprises the following steps:

an oxidation step (A): a step of oxidizing sec-butylbenzene to obtain an oxidation reaction liquid comprising sec-butylbenzene hydroperoxide as the main component, a concentration step (B): a step of concentrating the oxidation reaction liquid by distillation to obtain from the column bottom a bottom liquid comprising sec-butylbenzene hydroperoxide as the main component and from the column top a distillate comprising sec-butylbenzene as the main component, and recycling the distillate to the oxidation step (A), a decomposition step (C): a step of bringing the bottom liquid of the concentration step (B) into contact with an acidic catalyst to decompose sec-butylbenzene hydroperoxide thereby to obtain a decomposition liquid containing phenol and methyl ethyl ketone, the first neutralization step (D): a step of neutralizing the decomposition liquid with an aqueous alkali solution, separating the resulting liquid mixture into an oil layer and an aqueous layer, and recycling a part of the aqueous layer to the neutralization step (D), the first distillation step (E): a step of subjecting the oil layer obtained in the first neutralization step (D) to distillation to obtain a bottom liquid comprising phenol as the main component and a distillate comprising methyl ethyl ketone as the main component, an alkali-washing step (F): a step of washing the distillate obtained in the first distillation step (E) with an aqueous alkali solution to remove carboxylic acids, carboxylic acid esters, unsaturated ketones, and aldehydes, and then separating the resulting liquid mixture into an oil layer and an aqueous layer, the second neutralization step (G): a step of neutralizing the oil layer obtained in the alkali-washing step (F) and then separating the resulting liquid mixture into an oil layer and an aqueous layer, the first purification step (H): a step of subjecting the oil layer obtained in the second neutralization step (G) to distillation to obtain a bottom liquid comprising methyl ethyl ketone as the main component and an overhead liquid containing water, and the second purification step (I): a step of distilling the bottom liquid obtained in the first purification step (H) to recover methyl ethyl ketone as a bottom liquid and recycling a overhead liquid to the alkali-washing step (F).

2. The process according to claim 1 which further comprises the following step interposed between the second neutralization step (G) and the first purification step (H):

a washing step: a step of washing the oil layer obtained in the second neutralization step (G).

3. The process according to claim 1 wherein the first purification step (H) is a step of distilling the oil layer obtained in the second neutralization step (G) with a third substance called an entrainer added to the oil layer, to remove a liquid mixture containing water, acetone, and ethanol from the column top.

4. The process according to claim, 3 wherein the entrainer is hexane, cyclohexane, or heptane.

5. The process according to claim 1 wherein the second purification step (I) comprises the following steps:

the second distillation step (Ia): a step of distilling the bottom liquid obtained in the first purification step (H) to remove a tarry substance containing 3-methyl-3-buten-2-one as the bottom liquid, and the third distillation step (Ib): a step of distilling the overhead liquid obtained in the second distillation step (Ia) to recover methyl ethyl ketone, and recycling the newly obtained overhead liquid to the alkali-washing step (F).

6. The process according to claim 1 wherein the pH of the oil layer in the alkali-washing step (F) is 7–14.

7. The process according to claim 1 wherein the weight ratio of the oil layer to the aqueous layer in the alkali-washing step (F) is 0.5–10.

* * * * *